US00RE42377E

(19) United States
(12) Reissued Patent
Krall et al.

(10) Patent Number: US RE42,377 E
(45) Date of Reissued Patent: May 17, 2011

(54) COMPOSITION FOR CREATING VASCULAR OCCLUSIONS

(75) Inventors: Robert E. Krall, Santa Fe, NM (US); Charles W. Kerber, La Mesa, CA (US); Kimberly Knox, La Mesa, CA (US)

(73) Assignees: Stryker Corporation, Kalamazoo, MI (US); Stryker NV Operations Limited, Limerick (IE)

( * ) Notice: This patent is subject to a terminal disclaimer.

(21) Appl. No.: 11/827,668

(22) Filed: Jul. 12, 2007

Related U.S. Patent Documents

Reissue of:
(64) Patent No.: 6,037,366
Issued: Mar. 14, 2000
Appl. No.: 09/151,621
Filed: Sep. 11, 1998

U.S. Applications:
(63) Continuation of application No. 10/873,413, filed on Jun. 22, 2004, now abandoned, which is a continuation of application No. 09/823,775, filed on Mar. 30, 2001, now Pat. No. Re. 39,150.

(60) Provisional application No. 60/058,510, filed on Sep. 11, 1997.

(51) Int. Cl.
*A61K 31/275* (2006.01)
*A61K 31/12* (2006.01)
*A61K 31/05* (2006.01)
*A61K 33/24* (2006.01)
*A61K 33/42* (2006.01)

(52) U.S. Cl. ..... 514/527; 514/526; 514/558; 514/560; 514/690; 514/730; 514/824; 514/834; 514/930; 514/944; 514/970; 424/601; 424/605; 424/617; 424/649; 424/78.08; 424/78.31; 424/78.35; 424/78.37; 424/422

(58) Field of Classification Search ..... 514/526, 514/527, 558, 560, 690, 730, 824, 834, 930, 514/944, 970, 601, 605, 617, 649, 78.08, 514/78.31, 78.35, 78.37, 422; 424/601, 605, 424/617, 649, 78.08, 78.31, 78.35, 78.37, 424/422, 526, 527, 558, 560, 690, 730, 824, 424/834, 930, 944, 970; 604/49, 53
See application file for complete search history.

(56) References Cited

U.S. PATENT DOCUMENTS

| | | | | |
|---|---|---|---|---|
| 4,359,454 | A | 11/1982 | Hoffman | |
| 4,713,235 | A | 12/1987 | Krall | |
| 4,740,534 | A | 4/1988 | Matsuda et al. | |
| 5,328,687 | A | 7/1994 | Leung et al. | |
| 5,525,334 | A | 6/1996 | Ito et al. | |
| 5,624,685 | A | 4/1997 | Takahashi et al. | |
| 5,695,480 | A | 12/1997 | Evans et al. | |
| 5,702,361 | A | 12/1997 | Evans et al. | |
| 5,759,194 | A | 6/1998 | Hammerslag | |
| 5,795,331 | A | 8/1998 | Cragg et al. | |
| 5,981,621 | A | 11/1999 | Clark et al. | |
| 6,037,366 | A | 3/2000 | Krall et al. | |
| 6,143,352 | A | 11/2000 | Clark et al. | |
| 6,174,919 | B1 | 1/2001 | Hickey | |
| 6,476,069 | B2 | 11/2002 | Krall et al. | |
| 6,476,070 | B2 | 11/2002 | Krall et al. | |
| RE39,150 | E * | 6/2006 | Krall et al. | 514/527 |
| 2002/0018752 | A1 | 2/2002 | Krall et al. | |
| 2003/0194389 | A1 | 10/2003 | Porter | |

FOREIGN PATENT DOCUMENTS

| | | |
|---|---|---|
| EP | 0 664 104 | 7/1995 |
| WO | WO 99/42535 | 8/1999 |
| WO | WO 00/44287 | 8/2000 |

OTHER PUBLICATIONS

Almen, et al., "Basic Methdos of Investigative Neuroradiology" Chapter 6 in *Radiocontrast Agents* M. Sovak ed., Springer-Verlag Press, pp. 341-366 (1984).
Barr, John D., "Temporary and Permanent Occlusion of Cerebral Arteries," *Neurovascular Surgery 11(1)*:27-38 (2000).
Berthelsen, et al., "Embolization of Cerebral Arteriovenous Malformations With Bucrylate," *Acta Radiologica 31*:13-21 (1990).
Freeny, et al., "Transcatheter Therapy of Genitourinary Abnormalities Using Isobutyl 2-Cyanoacrylate(Bucrylate)," *AJR 133*:647-656 (1979).
Gobin, et al., "Treatment of Brain Arteriovenous Malformations by Embolization and Radiosurgery," *J. Neurosurg 85*:19-28 (1996).
Halbach, et al., "Preoperative Balloon Occlusion of Arteriovenous Malformations," *Neurosurgery 22(2)*:301-308 (1988).
Kerber, et al., "Liquid Acrylic Adhesive Agents in Interventional Neuroradiology," *Neuroendovascular Surgery 11(1)*:85-99 (2000).
Lefkowitz, et al.,"Balloon-Assisted Guglielmi Detachable Coiling of Wide-Necked Aneurysms: Part II—Clinical Results," *Neurosurgery 45(3)*:531-538 (1999).
Levy, Dr. David I., "Embolization of Wide-Necked Anterior Communication Artery Aneurysm: Technical Note," *Neurosurgery 41(4)*:979-982 (1997).
Malek, et al., "Balloon-Assist Technique for Endovascular Coil Embolization of Geometrically Difficult Intracranial Aneurysms," *Neurosurgery 46(6)*:1397-1407 (2000).
Mathis, et al., "Hydrophilic Coatings Diminish Adhesion of Glue to Catheter: an in Vitro Simulation of NBCA Embolization," *AJNR 18(9)*1087-1091 (1997).
The Merck Index, Merck & Co., Inc., Whitehouse Station, NJ, 1996, 12th ed., p. 647, item No. 3849.
Mericle, Robert A., M.D., "Temporary Balloon Protection as an Adjunct TI Endosaccular Coiling of Wide-Necked Cerebral Aneurysms," *Neurosurgery 41(4)*: 1992-1998 (1997).
Moret, et al., "The 'Remodeling Technique' in the Treatment of Wide Neck Intracranial Aneurysms," *Interventional Neuroradiology 3*:21-35 (1997).
Pelz, et al., "Preoperative Embolization of Brain AVMS With Isobutyl-2 Cyanoacrylate," *AJNR 9*:757-764 (1988).
Rao, et al., "Dissolution of Isobutyl-2 Cyanoacrylate on Long Term Follow Up," *AJNR 10*:135-141 (1989).

(Continued)

*Primary Examiner* — John Pak
(74) *Attorney, Agent, or Firm* — Vista IP Law Group LLP

(57) ABSTRACT

A composition including 2-hexyl cyanoacrylate and gold is useful in treating arteriovenous malformations (AVMs) and other body lumens to be blocked.

11 Claims, No Drawings

OTHER PUBLICATIONS

Spiegel, et al., "Adjusting the Polymerization Time of Isobutyl-2 Cyanoacrylate," *AJNR 7*:109-112 (1986).

Tseng et al., "Modified Ethoxyethyl Cyanoacrylate for Therapeutic Embolization of Arteriovenous Malformation," *Journal of Biomedical Materials Research 24*:65-77 (1990).

Vinuela, et al., "Dominant-Hemisphere Arteriovenous Malformations: Therapeutic Embolization With Isobutyl-2 Cyanoacrylate," *AJNR 4*:959-966 (1983).

Vinuela, et al., "Progressive Thrombosis of Brain Arteriovenous Malformations After Embolizations With Isobutyl 2-Cyanoacrylate,"*AJNR 4*:1233-1238 (1983).

Vinuela, et al., "Angiographic Follow-Up of Large Cerebral AVMS Incompletely Embolized With Isobutyl 2-Cyanoacrylate," *AJNR 7*:919-925 (1986).

Woodward, "Physiological and Biochemical Evaluation of Implanted Polymers," *Annals of the New York Academy of Sciences 146*:225-250 (1968).

* cited by examiner

COMPOSITION FOR CREATING VASCULAR OCCLUSIONS

Matter enclosed in heavy brackets [ ] appears in the original patent but forms no part of this reissue specification; matter printed in italics indicates the additions made by reissue.

This application claims the benefit of U.S. Provisional Application No. 60/058,510, filed on Sep. 11, 1997.

*More than one reissue application has been filed for the reissue of U.S. Pat. No. 6,037,366. This reissue Application is a continuation of U.S. application Ser. No. 10/873,413, filed Jun. 22, 2004, now abandoned, which in turn is a continuation of U.S. application Ser. No. 09/823,775, filed Mar. 30, 2001, now reissue RE39,150, which is a reissue of application Ser. No. 09/151,621, filed Sep. 11, 1998, now U.S. Pat. No. 6,037,366, which claims the benefit of U.S. Provisional Application No. 60/058,510, filed Sep. 11, 1997. Reissue application Ser. Nos. 11/827,668 (present application), 10/873,413 (abandoned) and 09/823,775 (RE39,150) are all reissue applications of U.S. Pat. No. 6,037,366.*

BACKGROUND OF THE INVENTION

1. Field of the Invention

This invention relates to a composition used to treat arteriovenous malformations ("AVMs") and other vascular abnormalities. The composition includes a cyanoacrylate liquid monomer and gold in a prepolymerized polymer of cyanoacrylate. The composition is placed into the body lumen via standard catheter procedures or directly percutaneously.

2. Description of the Related Art

AVMs and vascular tumors, especially those of the brain, are exceedingly difficult to treat. These growths may occur all over the body, but are especially difficult to treat when in the brain or brain stem. The composition of the invention is especially useful in treating neurological AVMs, but may also be used to treat tumors anywhere in the body.

Cyanoacrylate adhesives have been used surgically but are limited in their usefulness by cytotoxicity and heat generation. The brain is unusually sensitive to cytotoxicity and heat.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. § 1.56(a) exists.

SUMMARY OF THE INVENTION

The invention provides a composition that may be placed in a body lumen including veins and arteries by super selective catheterization or direct puncture using standard tools of the interventional angiographer. The composition of the invention has been successfully tested in simulated models of the AVMs and tumors under fluoroscopy and in systems that closely resembles the neurological condition of the human body. Further studies have been done in the pig rete. The rete is a body of fine arteries that allows the blood to flow into the pig brain which closely resembles normal human AVMs.

The composition is a cyanoacrylate which involves mixing two separate containers of the material immediately prior to administration of the material into the AVM by catheter. The composition may contain seven ingredients which are divided into two parts prior to mixture and use. It furnishes properties that are useful for closing neurological AVMs. The product can also be used to close any growth resembling an AVM in any part of the body. Because of the sensitive nature of the tissues in the brain, the general sensitivity of the product must be controlled. In less sensitive areas, the product will work equally as well.

Part I consists of a cyanoacrylate liquid monomer containing pure phosphoric acid (250 ppm) hydroquinone (100 ppm) and P-methoxyphenol (1200 ppm). This composition is stable and unchanging we believe for over two years. The container in which Part I is stored requires cleaning and preparation before such stability can be achieved. The liquid monomer of choice for this usage is 2-hexyl cyanoacrylate.

Part II consists of pure powdered gold (5±3 microns), a small amount of prepolymerized polymer of the same cyanoacrylate and ethyl myristate. Any of the large chain fatty acid esters will work to replace ethyl myristate so long as they are liquids.

The pre-polymerized polymers of cyanoacrylate are unstable and change their structures and properties even in the solid state. The change is exponential and therefore the polymer must be used within a limited amount of time before deterioration occurs.

The polymer is prepared by addition of part 1 to a rapidly stirring weak bicarbonate-water solution. The addition must be added drop-wise to avoid unpolymerized masses from forming. The solid polymer is washed thoroughly with pure water to remove any traces of bicarbonate, then washed thoroughly with pure methanol to remove the water. Methanol dries rapidly and when the polymer is further dried at a high reduced pressure for 16–18 hours, it is considered dry. The polymer must be used in the next step within 24 hours to obtain consistent results in the final product. This mixture must be sterilized within 72 hours from the time of preparation.

Part II is sterilized with ethylene oxide gas with the stopper held in an open position. Ethylene oxide is an alkylating agent and after sterilization the prepolymerized polymer is stable. Hence, the stability and sterilization of part 2 are carried out simultaneously. The sterilized samples of Part II are capped in a clean room under sterile handling conditions.

The pre-polymerized polymer can be stabled by treatment with any of the strong alkylating agents, like ethylene oxide, ketene, etc.

This composition of matter has good cohesion as well as adequate adhesion to function well for AVMs and other similar uses within the vascular tree. The cohesion keeps the material together during the time required for it to polymerize. The adhesion makes it stick to the artery walls.

The polymerized device will cause a modest but desirable inflammatory response in the treated tissues.

A Formulation for Arteriovenous Malformations and Tumors

It is desirable to prepare a formulation for the intravascular occlusion of AVMs and Tumors that will have the following properties:

- The product has a very slow rate of biodegradation.
- Both liquid and solid forms should have excellent cohesion.
- The delivered product should have medium adhesion
- The delivered product must be radiopaque.
- The solid polymer should be soft and pliable.
- The delivered product must have a very low or negligible histotoxicity.

The deposited product must have no long term negative properties such as carcinogenicity, teratogenicity, systemic toxicity or other unpredictable biological and medical effects.

The products must be sterile.

The delivered product must have good flow characteristics for selective catheterization.

The product must be stable on storage for an extended period of time.

The formulation should be made from pure products and be reproducible for simple manufacturing procedures.

The product formulation is:

| Part I (M1) | | |
|---|---|---|
| 2-Hexyl Cyanoacrylate | 999,550 | ppm |
| Hydroquinone | 100 | ppm |
| p-Methoxyphenol | 100 | ppm |
| Pure Phosphoric Acid | 250 | ppm |
| Part II (M2) | | |
| Pure Gold | 1.0000 | g |
| Pure Ethyl Myristate | 0.5000 | g |
| FMS* | 0.0200 | g |

*FMS is a specially prepared polymer of 2-hexyl cyanoacrylate and must be used within 24 hours of preparation or will change and be unusable. Further, it must be sterilized within 72 hours.

Each item of this formulation is critical to the proper performance of the product.

2-Hexyl Cyanoacrylate

This cyanoacrylate homolog was chosen because it biodegrades very slowly in blood or any living tissue. The secondary alcohol will biodegrade several thousand times slower than its primary derivative. This very slow degradation rate also lowers greatly the histotoxicity.

Hydroquinone

When the amount of hydroquinone is reduced by half (50 ppm) the product shows low shelf life stability. Large amounts over 100 ppm do not seem to effect the product stability. This inhibitor lowers the effect of the high energy free radicals that may appear in the cyanoacrylate.

p-Methoxyphenol

The slow polymerization of cyanoacrylates even under refrigeration is caused by low energy free radicals. When 100 ppm of p-methoxyphenol is present this slow polymerization is prevented and long term stability is achieved. Less p-methoxyphenol (50 ppm) will not protect the product.

Sulfur Dioxide

The faintest trace of sulfur dioxide is present in the product. One part per million can be seen and less is present. However, this very faint trace adds to the stability of Neuracryl* ml in the ampule.

Gold

Tantalum, platinum and gold are all radiopaque. Gold was best for us because it could be suspended colloidally in the mixture. One gram of gold is used per device.

Ethyl Myristate

Subbicates, fatty acid esters and other plasticizers, are useful for fastening the polymers of the cyanoacrylates. they also will stabilize the pre-formed polymers of the cyanoacrylates so that they may be used as thickeners. We have chosen ethyl myristate, an esterified, biocompatible fatty acid because of the convenience of purification and analysis and because is works well to give the formulation the desirable properties.

FMS

FMS is the polymer of 2-hexyl cyanoacrylate formed in a weak, aqueous sodium bicarbonate solutions. The polymer differs in structure and size depending on how it is formed. This polymer will remain stable until M2 can be formulated. The polymer must be formed and dried completely before use. The final formulation of M2 must occur within 24 hours because the ethyl myristate stabilized FMS until sterilization can be performed. After sterilization the product is stable for several years.

Neuracryl M

M1 and M2 are mixed immediately before use. The mixture should be used within 4 hours after mixing. If there is a delay, the syringe should be turned over several times a minute to resuspend the gold which will be settled.

What is claimed is:

[1. A composition for creating therapeutic vascular occlusions in an animal comprising a mixture of:

(a) Part 1 comprised of 2-hexyl cyanoacrylate, hydroquinone, p-methoxyphenol and phosphoric acid; and (b) Part 2 comprising gold metal powder, ethyl myristate and a sterilized polymer of 2-hexylcyanoacrylate in weak aqueous bicarbonate solution.]

[2. The composition of claim 1 wherein Part 1 comprises about 100 PPM hydroquinone, 100 PPM p-methoxyphenol, 250 PPM phosphoric acid and the remainder 2-hexyl cyanoacrylate.]

[3. The composition of claim 2 wherein Part 2 comprises about 65 percent by weight gold, about 30 percent by weight ethyl myristate and the remainder said sterilized polymer of 2-hexylcyanoacrylate in weak aqueous bicarbonate solution.]

[4. The composition of claim 1 wherein Part 2 includes sulfur dioxide as a stabilizer.]

[5. A method for creating therapeutic vascular occlusions in an animal needing therapeutic vascular occlusion comprising the steps of:

(a) Mixing together Part 1 comprised of 2-hexyl cyanoacrylate, hydroquinone, p-methoxyphenol and phosphoric acid with Part 2 comprising gold metal powder, ethyl myristate and a sterilized polymer of 2-hexylcyanoacrylate in weak aqueous bicarbonate solution; and (b) injecting the mixture into a vascular site needing occlusion with the gold metal powder suspended in the mixture.]

*6. A composition for creating therapeutic vascular occlusions in an animal comprising a mixture of:*

*(a) Part 1 comprising a cyanoacrylate liquid monomer, hydroquinone, p-methoxyphenol and phosphoric acid; and*

*(b) Part 2 comprising a radiopaque metal powder selected from the group consisting of gold, tantalum and platinum, a large chain fatty acid ester in liquid form and stabilized polymer of cyanoacrylate, wherein the cyanoacrylate is the same as the cyanoacrylate of Part 1.*

*7. The composition of claim 6, wherein the cyanoacrylate is 2-hexyl cyanoacrylate.*

*8. The composition of claim 6, wherein the vascular occlusion is created in an arteriovenous malformation (AVM).*

*9. The composition of claim 6, wherein the fatty acid ester is ethyl myristate.*

*10. The composition of claim 6, wherein Part 1 comprises 999,550 ppm 2-hexyl cyanoacrylate, 100 ppm hydroquinone, 100 ppm p-methoxyphenol and 250 ppm pure phosphoric acid.*

*11. The composition of claim 6, wherein Part 1 consists of a cyanoacrylate liquid monomer containing 250 ppm pure phosphoric acid, 100 ppm hydroquinone and 1200 ppm p-methoxyphenol.*

*12. A method for creating therapeutic vascular occlusions in an animal needing therapeutic vascular occlusion comprising the steps of:*

(*a*) *mixing together Part 1 comprised of cyanoacrylate liquid monomer, hydroquinone, p-methoxyphenol and phosphoric acid with Part 2 comprising a radiopaque metal powder selected from the group consisting of gold, tantalum and platinum, a large chain fatty acid ester in liquid form and a stabilized polymer of cyanoacrylate, wherein the cyanoacrylate is the same as the cyanoacrylate of part 1; and*

(*b*) *administering the mixture into a vascular site needing occlusion.*

*13. The method of claim 12, wherein the cyanoacrylate is 2-hexyl cyanoacrylate.*

*14. The method of claim 12, wherein the fatty acid ester is ethyl myristate.*

*15. The method of claim 12, wherein the vascular occlusion is created in an arteriovenous malformation (AVM).*

*16. The method of claim 12, wherein the administering is by catheter or by percutaneous methods.*

* * * * *